(12) United States Patent
Jalkanen et al.

(10) Patent No.: US 8,975,081 B2
(45) Date of Patent: Mar. 10, 2015

(54) BIOMARKER FOR MONITORING DEVELOPMENT OF DISEASES AND ASSESSING THE EFFICACY OF THERAPIES

(71) Applicant: Faron Pharmaceuticals Oy, Turku (FI)

(72) Inventors: Sirpa Jalkanen, Piispanristi (FI); Marko Salmi, Turku (FI); Markku Jalkanen, Piispanristi (FI); Mikael Maksimow, Turku (FI)

(73) Assignee: Faron Pharmaceuticals Oy, Turku (FI)

( * ) Notice: Subject to any disclaimer, the term of this patent is extended or adjusted under 35 U.S.C. 154(b) by 12 days.

(21) Appl. No.: 13/775,558

(22) Filed: Feb. 25, 2013

(65) Prior Publication Data

US 2013/0217033 A1   Aug. 22, 2013

Related U.S. Application Data

(63) Continuation-in-part of application No. 12/679,785, filed as application No. PCT/FI2008/050576 on Oct. 15, 2008, now abandoned.

(30) Foreign Application Priority Data

Oct. 24, 2007   (FI) ..................... 20070795

(51) Int. Cl.
*G01N 33/48* (2006.01)
*C12Q 1/44* (2006.01)

(52) U.S. Cl.
CPC ............. *C12Q 1/44* (2013.01); *G01N 2800/52* (2013.01)
USPC ................ 436/63; 435/7.1; 436/501; 424/9.2

(58) Field of Classification Search
None
See application file for complete search history.

(56) References Cited

U.S. PATENT DOCUMENTS

| | | | |
|---|---|---|---|
| 5,736,343 | A | 4/1998 | Landry |
| 7,534,423 | B2 | 5/2009 | Jalkanen |
| 7,772,192 | B2 | 8/2010 | Esko |
| 7,851,594 | B2 | 12/2010 | Presnell et al. |
| 2006/0198821 | A1* | 9/2006 | Jalkanen ........... 424/85.2 |

FOREIGN PATENT DOCUMENTS

| | | |
|---|---|---|
| WO | 0190403 A1 | 11/2001 |
| WO | 2004079013 A1 | 9/2004 |
| WO | 2007025044 A2 | 3/2007 |
| WO | 2007107598 A1 | 9/2007 |

OTHER PUBLICATIONS

Johnson, S.M. et al., "5'-Nucleotidase as a Marker of Both General and Local Inflammation in Rheumatoid Arthritis Patients," Rheumatology 1999; 38:391-396, copyright British Society for Rheumatology.
Airas, L. et al., "Mechanism of Action of IFN-β in the Treatment of Multiple Scierosis, A Special Reference to CD73 and Adenosine," Ann. New York Acadmey of Sciences 1110:641-648 (2007), copyright 2007 New York Academy of Sciences, doi: 10.1196/annals.1423.067.
Eckle, T. et al., "Identification of Ectonucleotidases CD39 and CD73 in Innate Protection during Acute Lung Injury," The Journal of Immunology, 2007, 178: 8127-8137, copyright 2007 by the American Association of Immunologists, Inc.
Thomson, L.F. et al., "Production and Characterization of Monoclonal Antibodies to the Glycosyl Phosphatidylinositol-Anchored Lymphocyte Differentiation Antigen Ecto-5'-Nucleotidase (CD73)," Tissue Antigens 1990: 35, 9-19, Publication No. 6040-IMM from the Department of Immunology, Research Institute of Scripps Clinic, La Jolla, CA.
Ueda, Y. et al., "Pravastatin Restored the Infarct Size-Limiting Effect of Ischemic Preconditioning Blunted by Hypercholesterolemia in the Rabbit Model of Myocardial Infarction," Journal of the American College of Cardiology, vol. 34, No. 7, 1999, pp. 2120-2125, copyright 1999 by the American College of Cardiology, Published by Elsevier Science Inc.
Zhou, Xuerui et al., "Effects of Ecto-5'-Nucleotidase on Human Breast Cancer Cell Growth In Vitro and In Vivo," Oncology Reports 17:1341-1346 (2007)., accepted for publication Feb. 20, 2007.
Farr, M. et al., "Source and Significance of 5-Nucleotidase in Synovial Fluid," Annals of the Rheumatic Diseases (1973), 32, 326-330, accepted for publication Dec. 11, 1972.
Hunsucker, S.A. et al., "The 5'-Nucleotidases as Regulators of Nucleotide and Drug Metabolism," Pharmacology and Therapeutics 107 (2005), pp. 1-24.
Airas et al., "OPL121, IFN-beta-treatmenet Augments Adenosine Production via CD73 (Ecto-5'-Nucleotidase) Upregulation Both on Cultured Endothelial Cells in vitro and in Multiple Sclerosis Patients in vivo," Multiple Sclerosis—Experimental & Neurobiology, Oral Platform Abstracts, Nov. 9, 2005, S77, 1 page.
English translation—in-part of Japanese reference, "Analysis of CD73 Expression in Esophageal Cancer," Journal of Japan Society of Clinical Oncology, 2005, vol. 40, No. 2, p. 548, PS16-1, 2 pages.
L De Groot et al., "Wegener's Granulomatosis: Disease Course, Assessment of Activity and Extent and Treatment," Lupus, 1998, vol. 7, pp. 285-291.
Mahanty et al., "Pathogenesis of Filoviral Haemorhagic Fevers," Lancet, 2004, vol. 4, pp. 487-498.

* cited by examiner

*Primary Examiner* — Gary W Counts
(74) *Attorney, Agent, or Firm* — Rothwell, Figg, Ernst & Manbeck P.C.

(57) ABSTRACT

The invention concerns a method for monitoring the development of a disease in a patient, and for assessing the efficacy of a therapy influencing on the CD73 level or activity in the patient, in particular a cytokine therapy or a statin therapy. CD73 in a tissue fluid drawn from the patient is used as a biomarker. The invention concerns also methods for determining of CD73 protein in a sample drawn from an individual's tissue fluid.

4 Claims, 8 Drawing Sheets

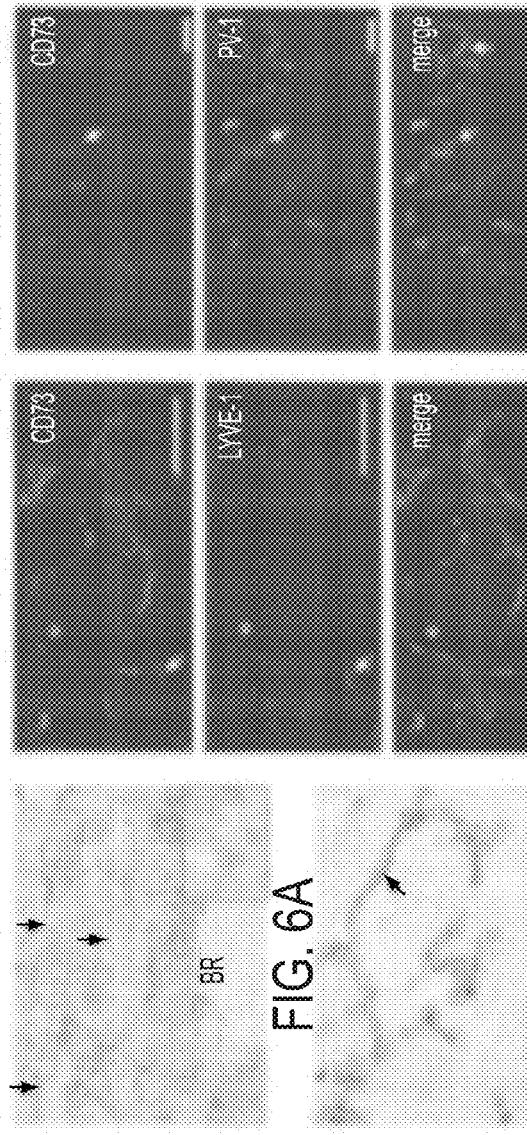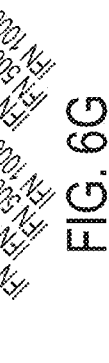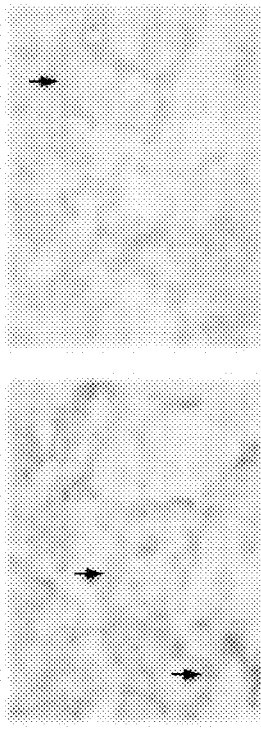

US 8,975,081 B2

BIOMARKER FOR MONITORING DEVELOPMENT OF DISEASES AND ASSESSING THE EFFICACY OF THERAPIES

CROSS-REFERENCE TO RELATED APPLICATIONS

The present application is a continuation-in-part of U.S. application Ser. No. 12/679,785, filed on 24 Mar. 2010, now abandoned, which in turn is a national stage filing under 35 U.S.C. §371 of PCT/FI2008/050576, filed 15 Oct. 2008, which in turn claims priority to FI20070795, filed 24 Oct. 2007, each of which are incorporated herein by reference.

FIELD OF THE INVENTION

This invention concerns the use of CD73 in tissue fluids as a biomarker for monitoring development of diseases and/or for assessing the efficacy of therapies. The invention concerns also methods for determining CD73 protein in a tissue fluid.

BACKGROUND OF THE INVENTION

The publications and other materials used herein to illuminate the background of the invention, and in particular, cases to provide additional details respecting the practice, are incorporated by reference.

CD73 is a cell-surface enzyme that has 5'-ectonucleotidase activity. It thus mediates the conversion of monophosphorylated purine nucleotides into corresponding nucleosides. For example, dephosphorylation of AMP to adenosine is catalyzed by CD73. CD73 is also present as a soluble form in the plasma and the soluble enzyme has the same enzymatic activity as the membrane bound form.

Adenosine is one of the physiological regulators of endothelial cell permeability [1, 2], and can thus be involved in the pathogenesis of many disorders like acute lung injury, systemic inflammatory response syndrome, acute respiratory distress syndrome, high-altitude sickness. Changes in endothelial permeability also take place in inflammation, in traumas and in cancer. CD73 controls endothelial permeability via an adenosine-mediated mechanism in normal conditions, hypoxia and ventilator-induced lung injury [3-7].

CD73 is induced by certain cytokines. Most importantly, interferon alpha and beta have been reported to increase the expression and activity of CD73 in humans (8, WO 2004/084933, 11). These cytokines are also clinically used to treat different diseases. Interferon alpha, for instance is used to treat certain infections and malignancies such as hepatitis and hairy cell leukemia. Interferon beta, on the other hand, is widely used to dampen inflammation in multiple sclerosis. However, in many cases the beneficial response to interferon treatment is only seen in a subpopulation of patients, and also the initially responding patients can later became refractory to the treatment. Thus, there is a need to develop easily measurable biomarkers that reflect the biological responsiveness of the body to the treatment.

The patent publication WO 2004/084933 discloses the use of cytokines for inducing endothelial CD73 expression and subsequently elevating the adenosine level in an individual. The use of interferon beta in combination with adenosine monophosphate (AMP) in the treatment of multi-organ failure in rats is described.

The patent publication WO 2007/042602 describes the use of plain interferon beta for treatment or prevention of ischemia reperfusion injury or multi-organ failure. Statins, hypolipidemic agents used to lower cholesterol level, are known to induce CD73 expression in the patients.

However, there is no disclosure in prior art concerning measuring CD73 protein in serum or any other tissue fluid for use as a biomarker for monitoring development of diseases or for assessment of efficacy of therapies.

SUMMARY OF THE INVENTION

We have shown that measurement of soluble CD73 activity can be used to monitor disease severity and responsiveness to the therapy. Therefore, we believe that analysis of CD73 expression level or activity by any technique may provide valuable information about the course of a disease or treatment response.

Thus, in one aspect this invention concerns a method for monitoring the development of a disease in a patient and for assessing the efficacy of a therapy influencing on the CD73 level or activity in said patient, wherein said disease is selected from the group consisting of
a) tissue trauma,
b) a reperfusion injury resulting from myocardial infarction or stroke, organ transplantations or an other surgical operation,
c) cancer or cancer metastasis, and
d) an inflammatory condition,
and wherein CD73 in a tissue fluid drawn from said patient is used as a biomarker, wherein the therapy
   is continued if the CD73 activity or level increases but is still below the level or activity indicating recovery of the patient,
   is replaced or supplemented by another therapy if the CD73 level or activity does not increase,
   is stopped if the CD73 level or activity has reached a level which is so high that it indicates recovery of the patient.

In another aspect, the invention concerns a method for determining of CD73 protein in a sample drawn from an individual's tissue fluid by
   i) quantifying the level of the CD73 protein in said sample by subjecting the sample to a binder recognizing the CD73 protein, and quantifying said binder, or by
   ii) detecting the activity of the CD73 protein in said sample by using thin layer chromatography or by subjecting said sample to a CD73 substrate, and monitoring the change of said substrate.

Figure 1:
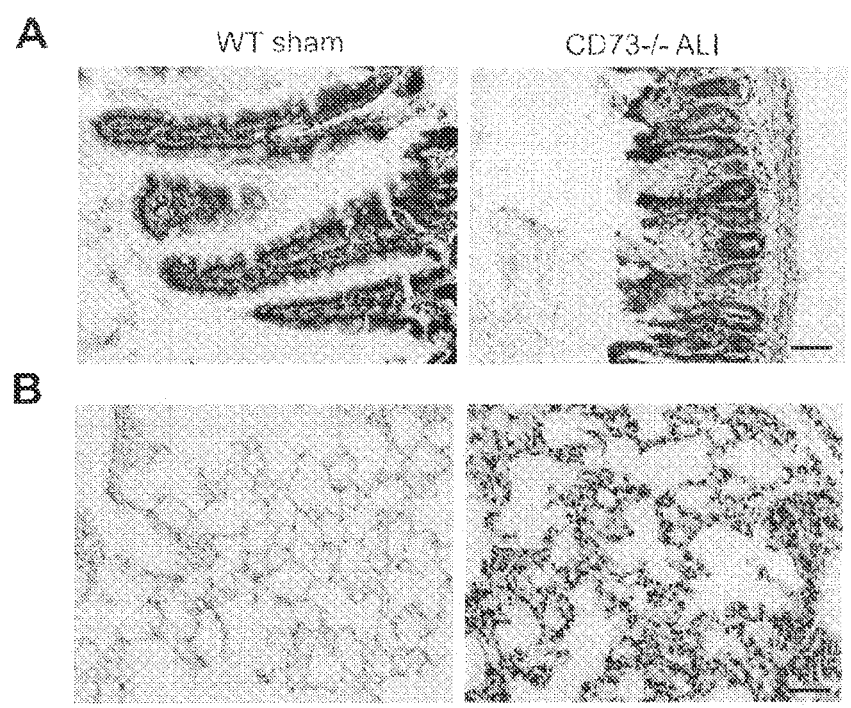
FIG. 1. The ischemia-reperfusion injury of the gut induces primary and secondary tissue damage. The mesenteric artery was occluded for 30 min and then allowed to be reperfused for 4 h. Representative micrographs from the (A) gut and (B) lungs of wild-type mice after sham operation (laparotomy only) and after induction of the IR-injury.

(Panels A and B) Immunoperoxidase stainings of a fresh human lung sample with the anti-CD73 antibody. The arrows point to the CD73 positive peri-bronchiolar (BR) vessels in panel A and to alveolar capillaries in panel B. Staining with a negative control antibody is shown in an inset in panel A. (Panel C) Double staining with anti-CD73 (green) and anti-LYVE-1 (red) recognizing lymphatic vessels. The lumen of a big lymphatic vessel is marked with an asterix. (Panel D) Double staining with anti-CD73 (red) and anti-PV-1 (green) recognizing blood vessels. Arrows point to some double positive vessels (yellow in merge panels) in panel C and D. (Panels E and F) A lung organ culture incubated with (Panel E) or without (Panel F) 1000 IU/ml of IFN-beta for 4 days and stained with anti-CD73. Arrows indicate some positive vessels. (Panel G) Summary of all organ culture experiments (N=4). The results are expressed as mean number of CD73 positive vessels/mm$^2$±SEM. (IFN-beta is marked IFN and the amount is in U/ml).

FIG. 7. Pharmacodynamic Markers, Soluble CD73 Activity, IL-6 Concentration and PaO$_2$/FiO$_2$ subsequent to IFN-beta treatment.

In dose escalation phase, patients were treated daily for six days with 0.44 mg (■), 4.4 mg (♦), 10 μg (▲) or 22 μg (●) of IFN-beta (N=3-5). A) Dose response of MxA protein levels. Patients treated with the optimal tolerated dose of 10 μg (N=26, B-H). Pharmacodynamic markers of IFN-beta MxA (B), Neopterin (C) and β2-microglobulin (D). E) Soluble CD73 activity and F) IL-6 concentrations. Geometric means±approximate standard errors are shown for each time point. Samples were taken just before dosing (day 1) and after each dose (day 2-7), follow-up samples were collected until day 14 (A-F). G) IL-6 concentrations are shown just before dosing (day 1) and after the third dose (day 4) for all patients who survived (white bars, N=34) and for patients who did not survive (black bars, N=3). H) PaO$_2$/FiO$_2$ levels during the treatment. PaO$_2$/FiO$_2$ levels are shown at screening, before and after the first and second doses and then up to day 28.

FIG. 8. Survival of IFN-beta Treated Patients Compared to Eligible Non-Treated Control Patients. Kaplan-Meier plots of all-cause mortality at day 28 of all IFN-beta treated patients (N=37, A) or patients treated with the OTD (N=26, B) in the clinical study (dashed line) compared to the eligible, non-treated control ALI/ARDS patients (59 patients, solid line).

Figure 9:
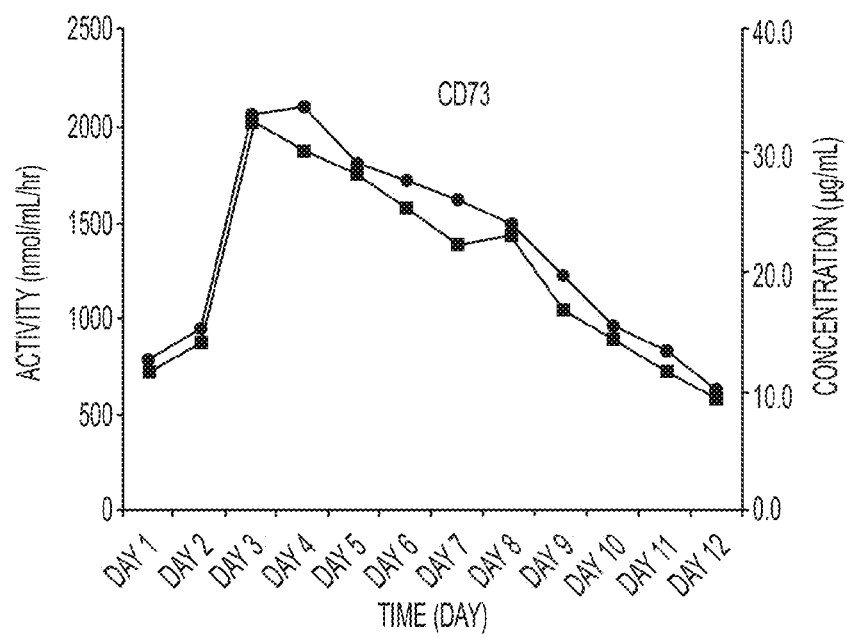

FIG. 9. shows both the activity and level (concentration) of soluble CD73 as function of time for one patient recovering from ALI or ARDS as an example. Soluble CD73 activity (■, left y-axis) and soluble CD73 concentration (●, right y-axis) were measured from aliquots of the same samples. FIG. 9 shows that activity and concentration measurements are comparable. One can see that CD73 (FIG. 9) and IL-6 (FIG. 7F) values show a dramatic change in the plasma concentrations, which correlates to the outcome of the patients.

DETAILED DESCRIPTION OF THE INVENTION

Definitions and Preferable Embodiments

The term "patient" or "individual" refers to a human or to an animal subject.

The term "monitoring the development of a disease" means that the progression of the disease (i.e. worsening of the disease) or the regression of the disease (i.e. a patient's recovery) can be made by comparing a measured level of the biomarker to a control or to one or more previous measurements, carried out at different points of time, of the level of the biomarker in the same patient. For example, a decreased level of the biomarker, compared to the result from a previous measurement or to a control may be used to indicate the progression of the disease, while an increased level of the biomarker, compared to the result from a previous measurement or to a control is used to indicate the regression of the disease. However, there are likely certain diseases affecting the level of the biomarker in the opposite way.

The term "tissue fluid" shall be understood to include any fluid which bathes and surrounds the cells. The term includes, for example, blood plasma, serum, lympha, urine, exudates (pleural, peritoneal) and cerebrospinal fluid.

The term "inflammatory condition" is meant to include any harmful and undesired inflammatory response in a tissue in an individual, wherein said inflammatory condition may result from an acute condition such as tissue trauma, a reperfusion injury resulting from myocardial infarction or stroke, organ transplantations or an other surgical operation, or from a chronic condition including allergic conditions, autoimmune diseases, and inflammatory diseases.

Diseases the development of which can be monitored by using CD73 protein in tissue fluid are typically selected from the group consisting of
a) tissue trauma,
b) a reperfusion injury resulting from myocardial infarction or stroke, organ transplantations or an other surgical operation,
c) cancer or cancer metastasis, and
d) an inflammatory condition.

Typical diseases leading to a change in the patient's CD73 level in tissue fluids, especially in serum are: tissue trauma; reperfusion injuries resulting from myocardial infarction or stroke, organ transplantations or other surgical operations; cancer or cancer metastasis; or inflammatory conditions resulting from the aforesaid traumas or reperfusion injuries or from chronic conditions including allergic conditions, autoimmune diseases, and inflammatory diseases. As examples of such chronic conditions can be mentioned arthritis, allergic conditions such as asthma, inflammatory conditions such as inflammatory bowel disease or an inflammatory condition of the skin, psoriasis, Parkinson's disease, Alzheimer's disease, autoimmune diseases, type I or type II diabetes, atherosclerosis, multiple sclerosis, Crohn's disease, or rejection reactions due to organ transplantations. Particularly, the inflammatory diseases systemic inflammatory response syndrome (SIRS), acute lung injury (ALI), acute respiratory distress syndrome (ARDS), multi-organ failure (MOF), ischemia reperfusion injury (IRI) and adverse drug reaction (ADRS) will lead to alterations of tissue fluid CD73 protein.

The therapy shall be understood to cover any therapy influencing on the CD73 level or activity in the patient. Important non-restrictive examples of such therapies are cytokine therapies and statin therapies.

The term "cytokine" includes any protein or peptide used in organisms as signalling compounds. In particular, this term refers to an interferon or an interleukin, but is not restricted thereto. In case the cytokine is an interferon, the interferon may be alpha-, beta-, gamma-, omega-, or any other interferon and it can be any subtype of the aforementioned interferons. Interferons are used in the treatment of the aforementioned diseases. As examples of interleukins can be mentioned IL-4, IL-10, IL-13 and IL-20.

"Statins" form a class of hypolipidemic agents used to lower cholesterol levels in individuals, particularly to reduce the risk of cardiovascular diseases. Also inflammatory conditions, dementia, cancer, nuclear cataract and pulmonary hypertension may respond to treatment with statins.

Determining of CD73 protein in a sample drawn from an individual's tissue fluid can be carried out by an immunodetection by quantifying the level of the CD73 protein in said sample by subjecting the sample to a binder recognizing the CD73 protein, and quantifying said binder.

Alternatively, the detection can be carried out by detecting the activity of the CD73 protein in said sample by using thin layer chromatography or by subjecting said sample to a CD73 substrate, and monitoring the change of said substrate.

The term "binder" shall be understood to include antibodies, which can be monoclonal or polyclonal or genetically engineered; any antibody fragments; aptamers and affibodies, and any other binder capable of binding to an epitope on the CD73 protein. CD73 antibodies are well known in the art, see for example http://www.biocompare.com/matrixsc/3194/6/67151/CD73.html. Affibodies represent a new kind of binders, small and especially stabile proteins, developed by Affibody Ab.

The binding assay can be competitive or non-competitive. One preferable assay is a sandwich assay where a capture antibody (or other kind of binder) immobilized to a solid support, is subjected to the sample comprising the antigen, which at a first epitope binds to the capture antibody and adding a labeled antibody (or other kind of binder), directed to another epitope of the antigen. The labeled antibody is quantified either directly (homogeneous assay) or after separation of non-immobilized labeled antibodies. The label can be a radioactive isotope, a fluorescent dye, an enzyme or any other detectable label.

For example, for the purpose of immunodetection, any suitable anti-CD73 specific antibody can be used to capture soluble CD73 from the sample, and then the amount of bound protein can be quantified using a variety of techniques. For instance, a sandwich ELISA can be employed in which one anti-CD73 antibody is immobilized to the bottom of multi-well plates, the sample is added, and the bound CD73 is detected using another anti-CD73 antibody. The anti-CD73 antibody is then detected using any of the multiple techniques suitable for antibody detection, such as labeled second-stage antibodies. The CD73 specificity of the reaction is controlled by including an irrelevant antibody as a capture or detection antibody and comparing the signals between these negative controls and anti-CD73 antibodies.

Determining of CD73 Activity:

CD73 activity can be measured using thin layer chromatography according to published protocols. CD73 activity can be also measured using any enzymatic assay that measures the conversion of AMP, or another purine mononucleotide that can be used as a CD73 substrate, into the corresponding nucleoside. For example, the assay can be based on conversion of radioactively or fluorescently labeled substrates. Detection methods can rely on the quantification of the decrease in a substrate concentration, or an increase in the product concentration or the release of the phosphate group. The CD73 dependence of the reaction can be determined by performing the assay in the presence and absence of a known CD73 inhibitor, such as AMPCP.

Suitable substrates for CD73 are, for example nucleoside-5'-monophosphates including adenosine-5'-monophosphate (AMP), inosine-5'-monophosphate (IMP), and the like.

The invention will be illuminated by the following non-restrictive Examples.

Example 1

Study of the Effect of IFN-Beta on Vascular Leakage in Animals Suffering from ALI ALI Model and Vascular Leakage $CD73^{-/-}$ mice, which were backcrossed to C57BL/6 background for 8 generations, and C57BL/6 wild-type (WT) mice were used. They lack CD73 mRNA, protein and enzyme activity [3]. The animals were weight-, sex- and age-matched. All mice had access to standard mouse chow and water until the experiment.

Mice were anesthesized with ketamine hydrochloride (100 mg/kg of body weight, i.p.) and xylazine (10 mg/kg of body weight, i.p.). During the anesthesia the mice spontaneously ventilated normal air. Before surgery animals received 1 ml of sterile saline subcutaneously to compensate for peroperative fluid loss. Superior mesenteric artery was dissected via midline laparotomy and occluded by microvascular clamp for 30 minutes. Sham animals underwent superior mesenteric artery dissection without vascular occlusion. The wound was sutured in one layer. The body temperature of the animals was maintained throughout the ischemia phase with a heating lamp. After the ischemia, the microvascular clamp was released, the wound sutured and animals received additional 1 ml of saline subcutaneously. After 235 minutes of reperfusion mice received FITC-conjugated dextran (25 mg/kg body weight in 0.2 ml sterile saline; mw. 70 000 D, Molecular Probes). Mice were sacrificed after 240 minutes of reperfusion and the tissue samples were collected. The 30 min ischemia-240 min reperfusion protocol is an established and reproducible ALI model. The protocol was approved by the Committee on Animal Ethics of Turku University (permission no: 1597/05 to Sirpa Jalkanen).

The effect of IFN-beta on CD73 activity and permeability was studied using pre- and post-treatment protocols. Subgroups of mice were pretreated with recombinant mouse IFN-beta (6000 IU s.c. once daily for 3 days prior to ischemia). In the post-treatment group, the animals got a single bolus of IFN-beta (20 000 IU) intravenously after the ischemic phase at the beginning of the reperfusion period.

All mice were injected i.v. with FITC-conjugated dextran (70 kDa) 5 minutes before euthanasia. Vascular leakage was determined from three color images taken from randomly chosen fields from cryosectioned lungs using computational image analysis (Image J).

Analyses of CD73 Activity

Ecto-5'-nucleotidase activity was assayed by TLC, as described previously [10]. Briefly, the standard enzyme assay contained in a final volume of 120 µl of RPMI 1640, lung lysate, 5 mmol/L β-glycerophosphate, and the indicated concentrations of AMP with tracer $[2-^3H]$AMP (sp. act., 18.6 Ci/mmol; Amersham, Little Chalfont, U.K.). Incubation times were chosen to ensure the linearity of the reaction with time, so that the amount of the converted AMP did not exceed 7-10% of the initially introduced substrate. Aliquots of the mixture were applied to Alugram SIL G/$UV_{254}$ TLC sheets (Macherey-Nagel, Duren, Germany) and separated with isobutanol/isoamyl alcohol/2-ethoxyethanol/ammonia/$H_2O$ (9:6:18:9:15) as solvent. $^3$H-labeled AMP and its dephosphorylated nucleoside derivatives were visualized in UV light and quantified using a Wallac-1409β-spectrometer. CD73 activity was expressed as nM of AMP hydrolyzed by milligram of protein per hour. Protein concentration in the lysates was determined by BCA Protein Assay Kit (Pierce, Rockford, Ill.) according to manufacturer's instructions.

Statistical Assays

Non-parametric one-way ANOVA (Kruskall-Wallis and Mann-Whitney U tests) were used.

Results

CD73 Activity Correlates with the Disease Activity

Figure 2:
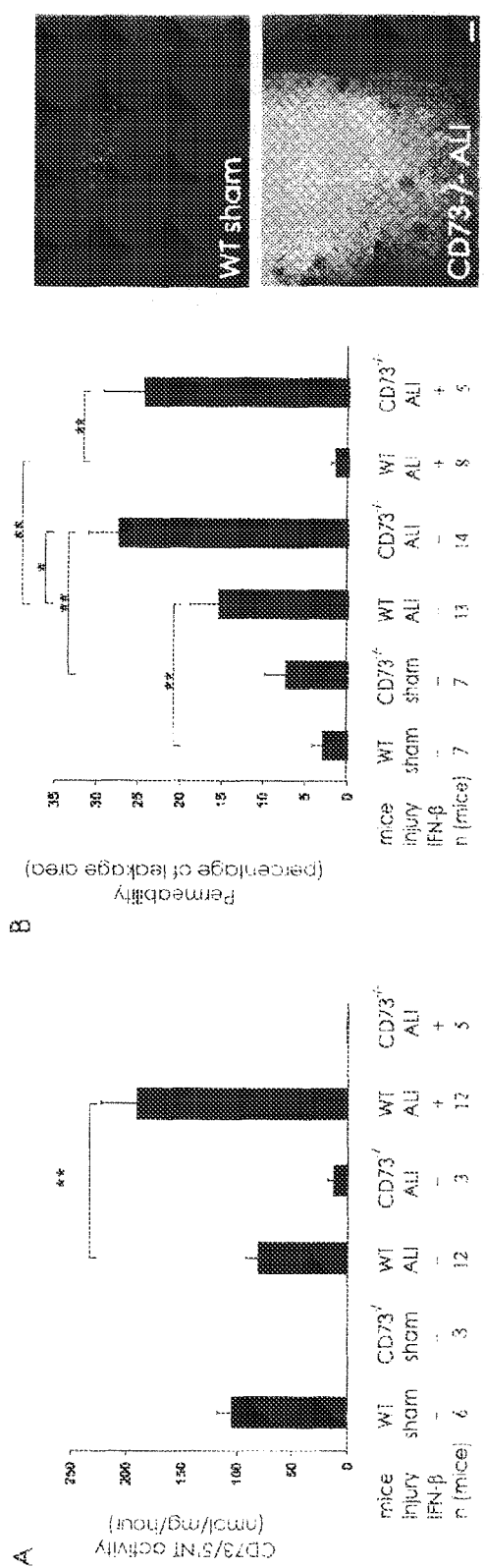
FIG. 2. Lung CD73/5'NT activity correlates inversely with the disease activity. CD73/5'NT$^{-/-}$ mice and their wild-type (WT) littermates underwent sham operation (sham) or 30 minutes of intestinal ischemia followed by 240 minutes of reperfusion (ALI). In additional groups, animals exposed to ALI were pretreated with interferon beta (IFN-beta). (A) Lung CD73/5'NT activity (mean±SEM, nmol of AMP hydrolyzed by milligram of protein per hour) measured from tissue lysates by TLC. (B) Semiquantitative analyses of vascular leakage (exudation of FITC-conjugated dextran) in lungs as measured from the histological sections using image analysis (% of section area exhibiting fluorescence above an arbitrarily chosen background value, mean±SEM). Representative micrographs from the indicated groups are also shown. Bar, 50 μm. *p<0.05, **p<0.01.

Intestinal ischemia-reperfusion (IR) caused marked tissue damage both in the gut and in the lungs (FIG. 1). In the lungs of the sham-operated wild-type mice the CD73 activity was low (FIG. 2A). The microscopic analyses of FITC-dextran in the lungs showed that there was only marginal leakage in WT mice undergoing sham operation (FIG. 2B).

When ALI was induced to wt animals, the CD73 activity was reduced by 25%. At the same time vascular leakage increased significantly. Changes in vascular permeability directly correlate to the disease severity, since the leakage of intravascular fluids to the lung parencyma and further to the alveoli is the major cause for deteriorating lung function and impaired gas exchange.

As expected, the CD73 activity was undetectable or at extremely low levels in CD73 deficient mice both after sham operation and after intestinal IR. In CD73 deficient mice the leakage in sham-operated animals was mildly increased when compared to the wild-type sham operated mice. Notably, when ALI was induced CD73 deficient mice showed about 80% more leakage in the lungs than their WT littermates ($p=0.03$).

These data show that there is an inverse correlation between the CD73 activity and vascular permeability, a measure of disease severity.

CD73 Activity Correlates with the Treatment Response

IFN-beta pretreatment for 3 days (at a dose clinically used in the treatment of multiple sclerosis) led to a 230% increase in CD73 activity in WT lungs during ALI ($p=0.002$, FIG. 2A). Most strikingly, the leakage area in WT mice after induction of ALI was reduced by more than 90% after the IFN-beta pretreatment when compared to non-treated littermates ($p=0.0001$, FIG. 2B). In fact, it was not different from animals undergoing only the sham operation. Strikingly, IFN-beta also had no protective effects on ALI in CD73 deficient mice. These data show that interferon beta treatment decreases vascular leakage in a strictly CD73 dependent manner. Moreover, increase in CD73 activity in wild-type mice can be used to predict beneficial outcome in response to IFN-beta treatment.

We then tested whether IFN-beta treatment could reverse an already established capillary injury. To that end we treated the mice with IFN-beta only after the ischemic period at the time of reperfusion. Notably, the single IFN-beta dose highly significantly improved vascular barrier function during the following 4 h reperfusion period. The leakage of FITC dextran was reduced by 90±9% in the post-treatment group when compared to the controls (n=8-13 mice/group, p<0.001). At the same time, CD73 activity measure from serum samples increased by more than 30% (from 427±22 in ALI group without treatment to 561±48 in ALI group treated with IFN-beta; p=0.04, n=4/group). Thus, the induction of CD73 activity correlates positively with a treatment response. Moreover, measuring CD73 activity in a blood sample can yield useful information about the IFN-beta responsiveness.

Example 2

Clinical study of the correlation between on-admission serum CD73 activity and the severity of the disease in patients with acute pancreatitis (AP)

Materials and Methods

Patients

The study consists of prospectively collected patients: 82 patients with acute pancreatitis (AP) all admitted to the emergency unit at Helsinki University Central Hospital between June 2003 and February 2007. Diagnosis of AP was based on typical clinical findings (acute onset of epigastric pain, nausea and vomiting) with elevated serum amylase concentration of at least three-fold the upper reference limit value and/or presence of computed tomography findings compatible with AP. The patients with a history of chronic pancreatitis were excluded from the study. The local research and medical ethics committee approved the study. Each patient or next 5 to kin were informed and gave consent.

Serum Samples

Serum samples were collected on admission to the hospital. The control samples (n=12) were collected from healthy laboratory personnel (age 32-56 years).

Determination of Serum CD73 (sCD73) Activity

The ecto-5'-nucleotidase activity in the sera was determined as previously described. In brief, serum (typically 10 μl) was incubated with 300 μM AMP along with tracer 3H-AMP (Amersham, UK) at 37° C. in a final volume of 60 μl RPMI1640 medium supplemented with 5 mM β-glycerophosphate. Use of a large excess of β-glycerophosphate as an alternative phosphorylated substrate in the enzyme assays allowed us to exclude the potential contribution of non-specific phosphatases (e.g. alkaline phosphatase) in the measured activities. The incubation times were chosen so that the amount of hydrolyzed AMP was less than 15% of the initially added substrate to ensure linearity. Sample aliquots were then applied to Alugram SIL G/UV254 sheets (Macherey-Nagel, Germany, and separated by TCL using isobutanol/isoamyl alcohol/2-ethoxyethanol/ammonia/H20 (9:6:18:9:15). $3^H$-labeled-AMP and its dephosphorylated nucleoside derivatives were visualized in UV-light and quantified by scintillation 3-counting. The CD73 activities in the sera are reported as nmolAMP hydrolyzed by one milliliter of serum in one hour. No ELISA-test for determining the protein levels of sCD73 is currently available.

Statistical Analysis

The results are given as medians, ranges and inter-quartile ranges (IQR). Comparisons between two groups were tested by the Mann-Whitney U test. When three groups were compared the Kruskall-Wallis test or the Jonkheere-Terpstra test for trend were used.

Results

Etiology and Severity of AP in the Study Population

All the included 82 patients were admitted to the hospital within 72 hours after the onset of pain. 50 patients with mild AP (grade 0) and 32 patients with severe AP according to Atlanta classification 34 were enrolled in the study. The patients with severe AP were further categorized into two subgroups. Grade 1 patients had only local complications including necrosis, pseudocyst or abscess, and they recovered without organ failure. Grade 2 patients developed organ failure (respiratory and/or renal failure). All of them developed respiratory failure and needed mechanical ventilation. Five (45%) of them also developed renal failure and needed hemodialysis. The etiology of the AP patients was alcohol in 59, gallstones in 15 and idiopathic/unknown in 8 cases (Table 1). All the patients survived.

TABLE 1

Characteristics of the Patients with Mild AP (Grade 0), Severe AP without Organ Failure (Grade 1) and Severe AP with Organ Failure (Grade 2)

|  | Grade 0 n = 50 | Grade 1 n = 21 | Grade 2 n = 11 |
|---|---|---|---|
| Female/male (n) | 16/34 | 6/15 | 0/11 |
| Age (y)* | 47 (19-87) | 49 (20-82) | 49 (30-62) |
| Etiology of AP (n) |  |  |  |
| Alcohol | 32 (64%) | 16 (76%) | 11 (100%) |
| Biliary | 11 (22%) | 4 (19%) | 0 |
| Idiopathic | 7 (14%) | 1 (4.8%) | 0 |
| Duration of symptoms (h)* | 24 (4-72) | 24 (12-72) | 24 (2-72) |
| Length of hospital stay (d)* | 4 (1-11) | 11 (6-41) | 29 (18-39) |
| Renal failure, n (%) | 0 | 0 | 5 (45%) |
| Respiratory failure, n (%) | 0 | 0 | 11 (100%) |
| Length of mechanical ventilation, d* | 0 | 0 | 16 (6-22) |
| SOFA, first day in hospital* | 0 (0-6) | 1 (0-8) | 2 (0-10) |
| SOFA, first day in ICU (grade 2) |  |  | 9 (3-12) |
| CRP on admission* (mg/l) | 12 (5-262) | 38 (3-426) | 35 (5-435) |
| Time from hospital admission to ICU admission (h) (grade 2)* |  |  | 24 (8-60) |

AP, acute pancreatitis; ICU, intensive care unit
*Median (range)

Increased sCD73 on Admission Correlates with Milder AP

Figure 3:
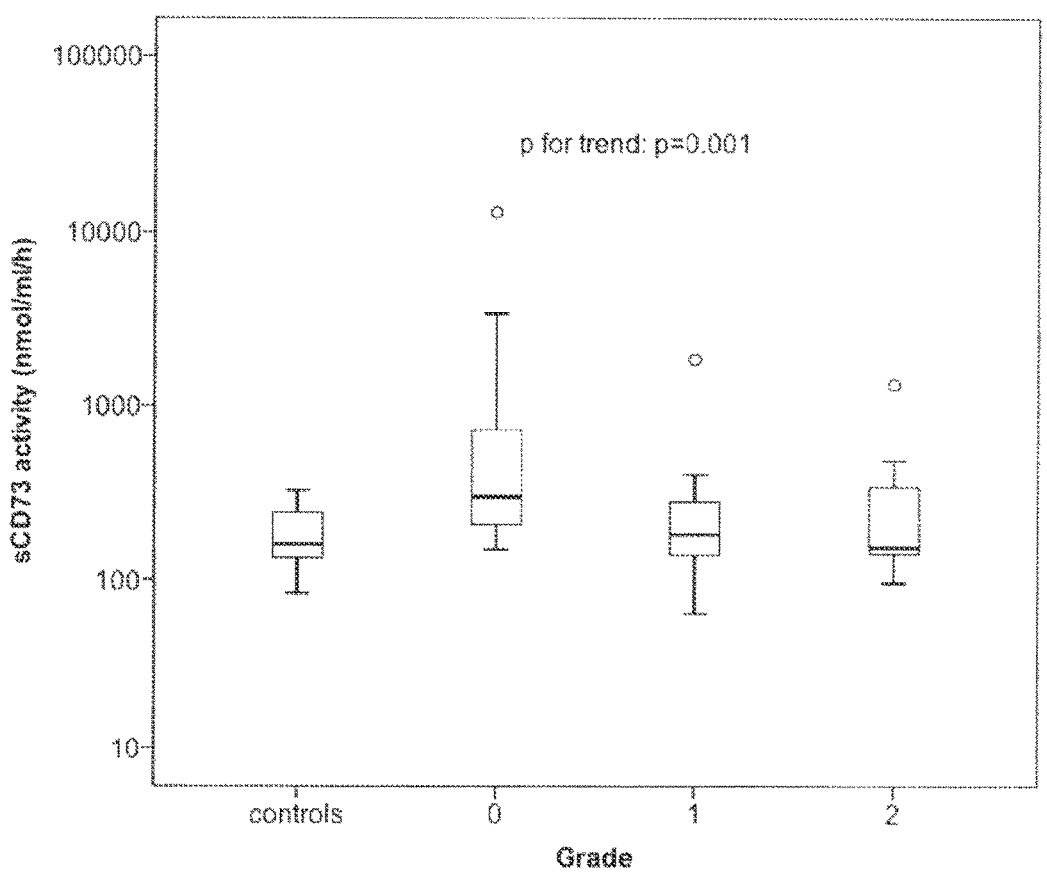
FIG. 3. On-admission levels of sCD73 in acute pancreatitis (AP) patients correlate with the severity of the disease. sCD73 activities were measured from sera of patients with mild AP (Grade 0, n=50), severe AP without organ failure (Grade 1, n=21), severe AP with organ failure (Grade 2, n=11), and healthy control subjects (n=12). Box-whisker plot shows median, inter-quartile range, highest and lowest values and outliers. Patients (n=82) differed significantly from healthy control subjects (P=0.006, Mann-Whitney U test). Jonkheere-Terpstra test was used to determine p for trend.
Figure 4:
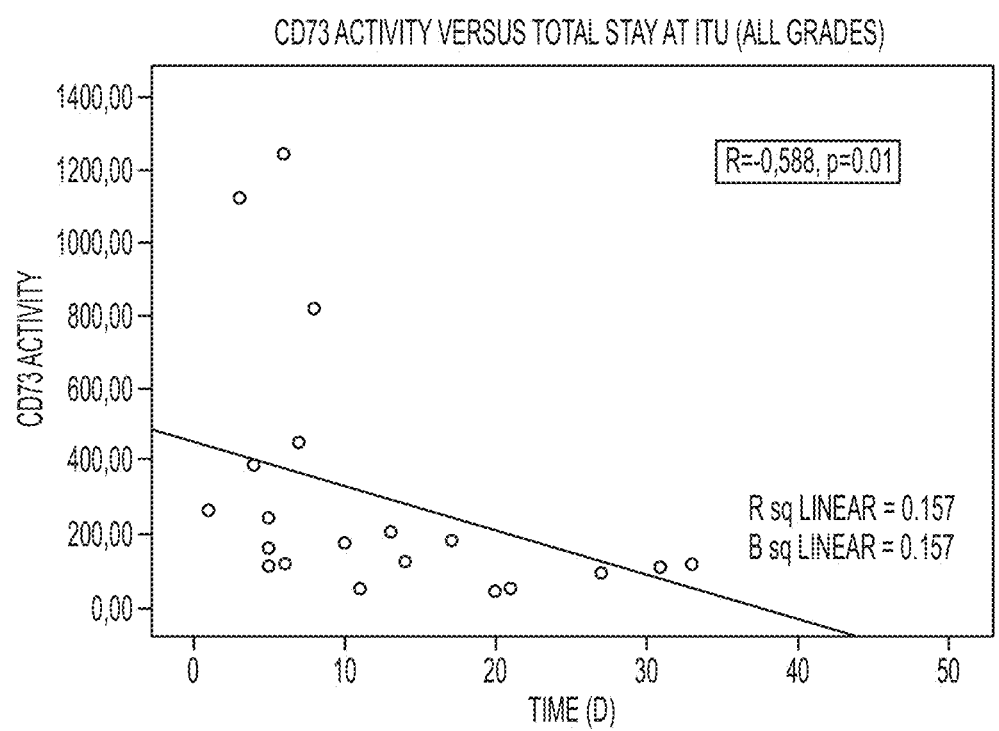
FIG. 4. CD73/5'NT activity versus total stay at intensive treatment unit (ITU) for patients with all grades of pancreatitis.

The activity of sCD73 in the sera of normal volunteers and 82 AP patients was determined using radioactive enzyme assays for 5'-nucleotidase activity. The median serum activity of sCD73 was higher in AP patients (273 nmol/ml/h, IQR 205-709) than in healthy controls (160 nmol/ml/h, IQR 130-250, P=0.006). Among the AP patients the sCD73 activity on admission correlated negatively with the severity grade of the developing AP (from grades 0 to 2 p-value for trend=0.001, FIG. 3). The sCD73 activity in patients with severe AP (grade 1+2, median 178 nmol/ml/h, IQR 134-326) was lower than in patients with mild AP (grade 0, median 300 nmol/ml/h, IQR 206-730, P<0.001).

The sCD73 level on admission was lower in patients who subsequently stayed in hospital more than 2 weeks (n=15) than in patients who stayed shorter time in the hospital (n=67) (167 nmol/ml/h, IQR=131-281 vs. 291 nmol/ml/h, IQR=190-610, P=0.008, Mann-Whitney U test).

Example 3

Effect of Intravenous Interferon Beta-1a on Lung CD73 Up-Regulation and Mortality in Patients with Acute Lung Injury (ALI) and Acute Respiratory Distress Syndrome (ARDS)

Materials and Methods:
Immunohistochemistry and Human Lung Organ Cultures

Ethical permission was obtained from the legal authorities at University Hospital in Turku for lung biopsies to be taken from macroscopically and microscopically normal looking areas of lung resections. Frozen sections of untreated samples and samples cultured with and without 500 and 1000 IU/ml IFN-beta 1a (Rentschler Biotechnologie) for 1 and 4 days were stained with anti-CD73(4G4) or class-matched negative control antibody followed by FITC-anti-mouse IgG (Sigma) or HRP conjugated anti-mouse IgG (DAKO). Diaminobenzidine was used as a chromogen. Scoring of CD73 positive vessels was performed in each condition using immunofluorescence stained sections and on average 20 fields/sample was counted with 200× magnification. Double stainings were performed as indicated in Table 2.

TABLE 2

Staining Schemes
Antibodies used

| First step | Second step | Third step | Fourth step |
|---|---|---|---|
| anti-CD73 (4G4*) | HRP-anti-mouse IgG |  |  |
| neg co (3G6) | HRP-anti-mouse JgG |  |  |
| anti-CD73 (4G4) | Alexa488-anti-mouse IgG1 | anti-LYVE† | Alexa546-anti-rabbit IgG |
| neg co (3G6) | Alexa488-anti-mouse IgG1 | normal rabbit serum | Alexa546-anti-rabbit IgG |
| anti-CD73 (4G4) | Alexa546-anti-mouse IgG1 | anti-PV-1(PAL-E)‡ | Alexa488-anti-mouse IgG2a |
| neg co (3G6) | Alexa546-anti-mouse IgG1 | mouse IgG2a | Alexa488-anti-mouse IgG2a |

*reference 1
†Reliatech
‡Abcam

Intravenous Formulation of Interferon Beta-1a

The investigational medicinal product (IMP) used in the clinical trial was human recombinant interferon beta from Merck Serono (Geneva, Switzerland). For the trial, this product (Rebif®) was formulated for an intravenous use, released and distributed to the hospital pharmacies by Chester Medical Solutions (Bromborough, UK). The IMP for each dose (0.44 μg, 4.4 μg, 10 μg and 22 μg) was diluted with 0.9% sterile saline to equal relative volumes at the bed site and administered immediately intravenously to the study patient. The dose regimen consisted of daily equal amounts of IMP for six days and the first dose was administered within 48 hours of ALI/ARDS confirmation. The IFN-beta used with isolated human lung tissues was based on Rentschler Biotechnologie (Laupheim, Germany) produced IFN-beta 1a from CHO cells.

Clinical Study Design for IFN-Beta Study

The IFN-beta study design was approved by UK regulatory authorities (MHRA, London, UK) and consisted of open-label, dose escalation (cohorts 1-4) and a dose expansion (cohort 5) phases (Table 3). Eligible were patients aged ≥18 years with ALFARDS (bilateral pulmonary infiltrates, P/F ratio≤40 kPa, no evidence of raised left atrial pressure) being treated with assisted ventilation. Excluded were those who were pregnant, had previously received IFN-beta, were receiving immuno-modulatory therapy, or who were suffering from burns, lung cancer or lung metastases, chronic obstructive pulmonary disease, chronic renal failure, renal dialysis or heart failure.

TABLE 3

Patient Demography and Efficacy End Points.*

| | 0.44 µg Cohort 1 (N = 3) | 4.4 µg Cohort 2 (N = 3) | 10 µg Cohort 4 (N = 4) | 22 µg Cohort 3 (N = 5) | 10 µg Cohort 5 (N = 22) |
|---|---|---|---|---|---|
| AGE | | | | | |
| Median (years) | 48 | 34 | 37.5 | 52 | 55 |
| range (min/max) | (44/83) | (18/64) | (31/67) | (35/67) | (26/79) |
| SEX (males) | 2/3 | 2/3 | 3/4 | 4/5 | 11/22 |
| Primary aetiology of ALI/ARDS | | 1/3 | | | 1/22 |
| Trauma | 1/3 | 1/3 | 1/4 | 1/5 | 8/22 |
| Sepsis | 2/3 | 1/3 | 1/4 | 1/5 | 4/22 |
| Aspiration | | | 1/4 | 2/5 | 9/22 |
| $PaO_2/FiO_2$ (kPa) | | | | | |
| Median at Screening | 18 | 26 | 18.5 | 19 | 19.7 |
| range (min/max) | (18/22) | (12/34) | (15/38) | (12/23) | (7/36) |
| APACHE II † | | | | | |
| Median at Screening | 25 | 15 | 16 | 22 | 23 |
| range (min/max) | (21/31) | (12/17) | (11/18) | (15/33) | (15/43) |
| SAPS | | | | | |
| Median at Screening | 55 | 34 | 30 | 35 | 43 |
| range (min/max) | (47/60) | (31/66) | (17/41) | (32/67) | (18/99) |
| MMS | | | | | |
| Median at Screening | 3.5 | 2.3 | 2.9 | 2.8 | 2.6 |
| range (max/min) | (2.8/3.5) | (2.3/4.0) | (2.5/3.3) | (1.5/3.0) | (1.3/4.0) |
| Time to treatment (hours) | | | | | |
| Median | 33.9 | 36.6 | 44.5 | 32.7 | 30.7 |
| range (min/max) | (18.0-44.3) | (31.4-45.2) | (33.1-47.2) | (3.1-47.5) | (5.5-47.5) |
| Day 28 Mortality | 1/3 | 0/3 | 0/4 | 0/5 | 2/22 |
| Month 6 Mortality | 1/3 | 0/3 | 0/4 | 0/5 | 3/22 |
| Days Alive at Day 28 | | | | | |
| Median | 28 | 28 | 28 | 28 | 28 |
| range (min/max) | (10/28) | (28/28) | (28/28) | (28/28) | (5/28) |
| Days on ITU | | | | | |
| Median | 28 | 22 | 10.5 | 16 | 28 |
| range (min/max) | (28/28) | (3/28) | (7/28) | (14/21) | (3/28) |
| Days Alive and off Ventilation | | | | | |
| Median | 0 | 9 | 21 | 17 | 5 |
| range (min/max) | (0/8) | (0/26) | (0/24) | (10/21) | (0/26) |
| Days on Vasoactive Drugs | | | | | |
| Median | 1 | 2 | 1 | 3 | 4 |
| range (min/max) | (0/23) | (2/10) | (0/10) | (0/6) | (0/28) |
| Vasoactive | 2/3 | 3/3 | 2/4 | 2/5 | 13/22 |
| Renal Support | | | 1/4 | | 5/22 |

APACHE II: Acute Physiology And Chronic Health Evaluation II, SAPS: Simplified Acute Physiology Score, MMS: Modified Murray Score.
*Values are shown as median values with range within each treatment cohort and for all study patients.
† APACHE II scores were available from 36 treated patients (25 on OTD). APACHE II classification system is shown with the respective death ratio and the patient distribution within the classification system is indicated.

Figure 5:
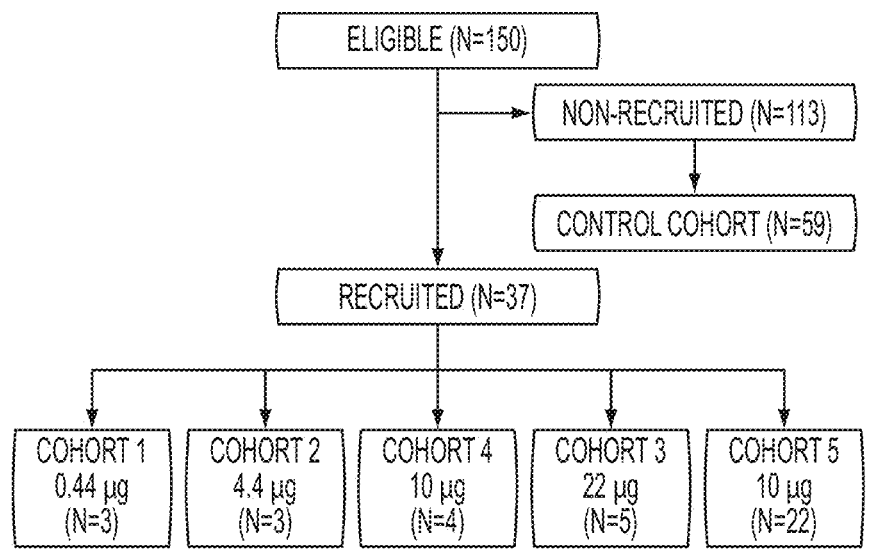
FIG. 5. Distribution of the eligible patients to different cohorts in IFN-beta clinical study FIG. 6. CD73 Is Expressed Both in Blood and Lymphatic Vessels of Lungs and Is Up-Regulated by IFN-beta.

Recruitment was conducted in eight UK Intensive Care Units between February 2009 and April 2011. A total of 150 patients met the inclusion criteria, of whom 37 were entered into the study (Cohort diagram shown as FIG. 5). Those not recruited included suitable subjects whose availability coincided with the 'safety-window' periods (see below). Fifty-nine such non-recruited subjects from two of the most active sites (St Mary's Hospital and University College London Hospital) were included as controls, after ethical permission was retrospectively granted (11/LO/1575) for use of their anonymised demographic and outcome data.

Patients received a daily intravenous dose of IFN-beta for 6 days and were followed for 28 days, with further assessment of all-cause mortality at 6 months. Dose escalation (phase I) tested safety and tolerability of IFN-beta in order to identify an optimal tolerated dose (OTD). A safety period excluded recruitment for 21 days at all sites after the first patient was enrolled at each new dose and led to 59 non-recruitable patients at the two most active recruiting sites. The OTD was subsequently used in the dose expansion phase (phase II), which also tested the impact of IFN-beta on 28-day all-cause mortality as the primary end point.

Sample Analysis

Serum samples were collected (two hours before each dose and daily thereafter until day 14), then separated and frozen for subsequent batch analysis. Serum concentrations of the known IFN-beta response markers MxA, neopterin and beta-2-microglobulin were measured using in-house or commercial assays. Evidence of impact on the inflammatory state was sought through assay of serum levels of the pro-inflammatory cytokine interleukin-6 (IL-6). Evidence of impact on CD73 expression was sought by measurement of its serum enzymatic activity, using thin layer chromatography.

Statistical Analyses

Differences between cohorts were tested using Mann-Whitney U test for continuous variables and chi-squared or Fisher's exact test for categorical variables, with results presented as median with interquartile range or percentage. Biomarkers were log-transformed before analysis to obtain a normal distribution. Changes over time were assessed using a random intercept model to take account of the correlations of measurements within subject. Time was fitted as a fixed effect factor. Coefficients from the model were exponentiated in order to express changes as the percentage change from baseline. Biomarker levels at each time point are presented as geometric mean and approximate standard error. In addition, we calculated the area under the curve (above the baseline value) for each patient using the trapezoid rule. Associations between biomarkers were assessed by Spearman rank correlation. Differences in death rates were assessed using exact logistic regression because of the small number of deaths. Odds ratios (OR) and 95% confidence intervals were obtained with and without adjustment for age, gender and APACHE-II score. Survivor functions were plotted using Kaplan-Meier plots with differences tested by log-rank test. P value P≤0.05 was considered significant.

Results

Human Lung CD73 Expression in Response to IFN-Beta

Exposure of human lung to IFN-beta increased CD73 expression in pulmonary capillary endothelium and lymphatic vasculature. The response was both time- and dose-dependent: 1000 U/ml of IFN-beta increased the expression 4- and 14.3-fold on days 1 and 4 respectively, P=0.04 and 0.004, when measured as the number of CD73 positive vessels (FIG. 6).

Clinical Study of IFN-Beta in ALI/ARDS Patients

The primary ARDS/ALI aetiology and clinical characteristics of patients (60% male; median age 52 [range 18-83]; median P/F ratio 19 [IQR 14-24]; Acute Physiology and Chronic Health Evaluation II [Apache II] median score 21.5 [IQR 17-26]) did not differ from those in controls (Table 4).

TABLE 4

Patients on OTD, All Patients and Eligible Control Cohort Patients demography and Day 28 Mortality*.

|  | All on OTD N = 26 | All patients N = 37 | Control Cohort N = 59 |
|---|---|---|---|
| Age |  |  |  |
| Median | 55 | 52 | 61 |
| [range] | [26-79] | [18-83] | [19-81] |
| P value vs. controls | P = 0.27 | P = 0.10 | — |
| Sex % |  |  |  |
| male | 53.9% (14/26) | 59.5% (22/37) | 61.0% (36/59) |
| P value vs. controls | P = 0.54 | P = 0.88 | — |
| PaO$_2$/FiO$_2$ (kPa) |  |  |  |
| Median | 19.7 | 19 | 18.8 |
| [IQR] | [12.8-25.8] | [14-24] | [12.5-25] |
| P value vs. controls | P = 0.51 | P = 0.44 | — |
| APACHEII † |  |  |  |
| Median | 22 | 21.5 | 23 |
| [IQR] | [17-27] | [17-26] | [18-29] |
| P value vs. controls | P = 0.34 | P = 0.24 | — |
| APACHEII distribution |  |  |  |
| 0-4 | 0 | 0 | 0 |
| 5-9 | 0 | 0 | 1 (1.7%) |
| 10-14 | 1 (4.0%) | 2 (5.6%) | 5 (8.5%) 1 ‡ |
| 15-19 | 10 (40.0%) | 13 (36.1%) | 15 (25.4%) 5 |
| 20-24 | 6 (24.0%) 1 | 10 (27.8%) 1 | 13 (22.0%) 4 |
| 25-29 | 4 (16.0%) 1 | 5 (13.9%) 2 | 13 (22.0%) 4 |
| 30-34 | 3 (12.0%) | 5 (13.9%) | 8 (13.6%) 2 |
| >34 | 1 (4.0%) | 1 (2.8%) | 4 (6.8%) 3 |
| P value vs. controls | P = 0.82 | P = 0.91 | — |
| Day 28 mortality | 7.7% (2/26) | 8.1% (3/37) | 32.2% (19/59) |
| P value vs. controls | P = 0.02 | P = 0.01 |  |

APACHE II: Acute Physiology And Chronic Health Evaluation II, SAPS: Simplified Acute Physiology Score, MMS: Modified Murray Score.
*Values are shown as median values with range within each treatment cohort and for all study patients.
† APACHE II scores were available from 36 treated patients (25 on OTD). APACHE II classification system is shown with the respective death ratio and the patient distribution within the classification system is indicated.
‡ Number (percentage) of patients, bold: number of actual deaths falling to different APACHE scores.

Optimal Tolerated Dose of IFN-Beta in ALI/ARDS Patients

A total of 37 patients were treated with IFN-beta, 15 during the dose escalation and 22 during the dose expansion phases. In the dose expansion phase, two patients received only three and five doses, respectively, due to a rapid clinical improvement, which led to extubation and discharge from the ICU.

Figure 7A:
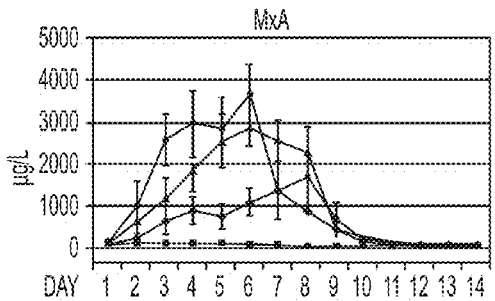
Figure 7B:
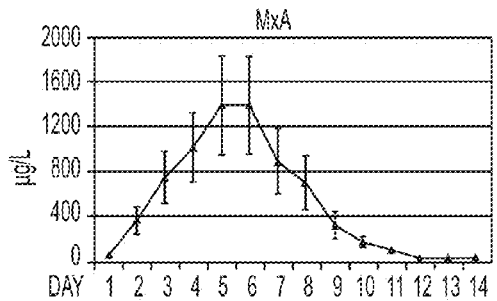
Figure 7C:
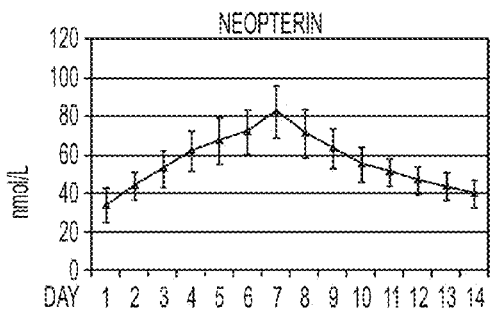
Figure 7D:
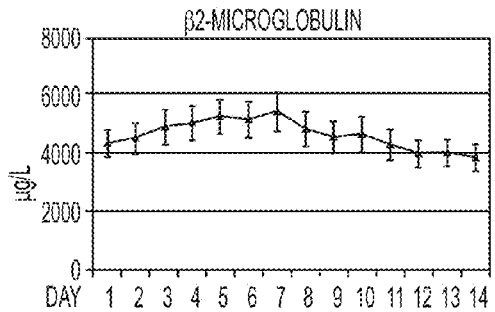
Figure 7E:
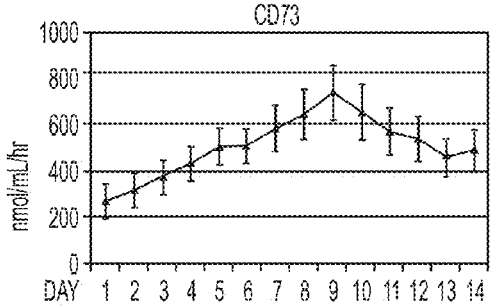

Cohorts 1-4 represented dose escalation of IFN-beta from a daily dose of 0.44 µg to a maximum of 22 µg for six days. No drug-related toxicity was observed with daily doses of 0.44, 4.4 and 10 µg. However, two out of the five patients receiving the highest dose (22 µg/day) experienced adverse events (fever, rigors and tachycardia), which did not appear during the first 2 doses, but became evident during the following doses, and which ceased when IFN-beta administration was stopped. Further use of this dose was thus prohibited and, in accordance with the study design, the next highest dose was chosen for the escalation stage. None of the additional 22 patients treated with 10 µg/day dose in phase II showed any systemic drug related adverse events. Serum MxA concentrations rose substantially in response to the 10 µg daily dose, this response being no greater with administration of 22 µg IFN-beta dose (FIG. 7A). Levels decreased rapidly upon cessation of therapy. Together, these data support 10 µg/day as being an optimal dose. The MxA values rose from 68.6±21.2 to 1389.1±434.7 µg/L, a 20 fold increase (95% CI 10.8 to 38.0) p<0.0001), a biological response to IFN-beta being confirmed by the rise in neopterin (from 34.3±5.5 to 82.5±13.4 nmol/L, a 2.4 fold increase (95% CI 2.0 to 2.9) P<0.00001) and beta-2-microglobulin from 4331.4±539.6 to 5349.3±681.2 µg/L, an increase of 24% (95% CI 8% to 41%, P=0.002). This biological response extended to induction of CD73: while ethical considerations precluded sampling lung tissue to monitor CD73 levels in patients, activity of serum CD73 rose steadily in response to treatment, reaching a peak shortly after the final dosing (from 265.0±43.3 to 732.5±129.8 nmol/ml/h, a 2.8 fold increase [95% CI 2.1 to 3.64, P<0.0001]). Kinetics of these markers is shown in FIG. 7 (B-E) for all optimal-tolerated dose patients.

Clinical Outcome of IFN-beta Treated ALI/ARDS Patients

Figure 7F:
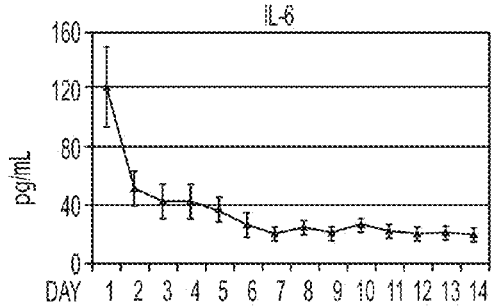
Figure 7G:
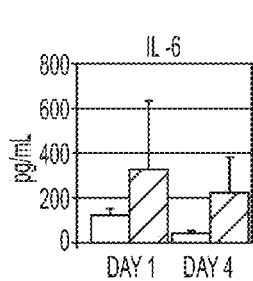
Figure 7H:
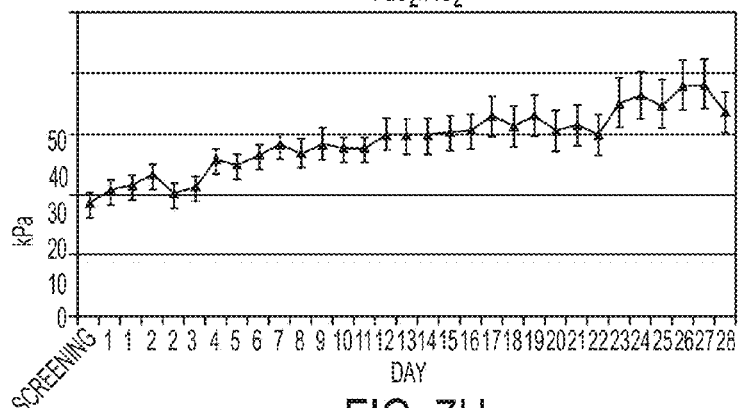

IL-6 is a well known pro-inflammatory cytokine, whose serum concentration have been shown to correlate with poor survival in ALI/ARDS. Our data are supportive of such an association: whilst the circulating concentration of IL-6 fell with treatment in the 10 µg/day dose-group overall (from 121.8±27.8 to 25.9±6.1 pg/ml by day 6, a decrease of 78.8% (95% CI: 68.4 to 85.7, p<0.0001), this reduction was greater amongst the survivors (FIG. 7F,G). Statistical confirmation of this difference was not feasible given the paucity of deaths. Administration of IFN-beta was associated with a steady improvement in P/F ratio (18.5±1.4 to 33.4±3.6 kPa, p=0.002). Kinetics for phase II shown in FIG. 7F,H).

Figure 8A:
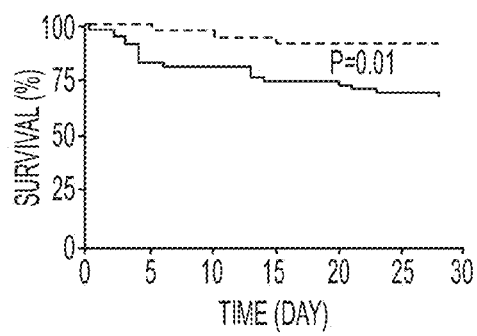
Figure 8B:
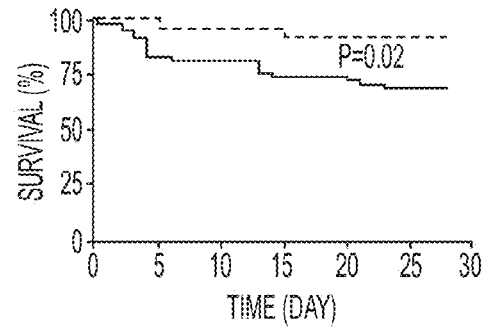

Treatment with IFN-beta was also associated with a substantial improvement in 28-day mortality, when compared to untreated control subjects. The control cohort had a mortality of 32.2% (19/59), in keeping with that the expected death rate of <40% for an ARDS cohort having Apache II scores of 20-24 (Table 4). By comparison, only three of the 37 treated (8.1%) patients died (FIG. 8A). The group that received 10 µg/day had a mortality of 7.7% (2/26). Thus, treatment with IFN-beta was associated with a significant 81% reduction in odds of mortality (OR [95% CI] 0.19 [0.03 to 0.72], p=0.01: FIG. 8A). The difference in mortality between the group receiving the optimal-tolerated dose of IFN-beta (2/26) and the control cohort was also significant (OR [95% CI] 0.18 [0.02 to 0.85], p=0.02: FIG. 8B). The APACHE II scores for those who died are shown in Table 4. These results remained significant after adjustment for age, gender and APACHE-II score. Similarly, only 8.7% (2/23) from the IFN-beta treated patients in the same hospitals, where the control cohort was collected died (p<0.04).

Example 4

In another study, soluble CD73 activity was measured from samples of one of the treated patients in the above mentioned study at indicated time points (see FIG. 9) using the previously published thin layer chromatography based technique from a patient showing very strong induction in soluble CD73 levels. The soluble CD73 concentration was measured by an ELISA assay based on the use of a capture antibody and a detection antibody in a sandwich assay. The activity and concentration of the soluble CD73 were measured from aliquots of the same samples. FIG. 9 shows that the soluble CD73 activity and concentration behave similarly.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

1 Hasko, G. and Cronstein, B. N., Adenosine: an endogenous regulator of innate immunity. *Trends Immunol.* 2004. 25: 33-39.
2 Ohta, A. and Sitkovsky, M., Role of G-protein-coupled adenosine receptors in downregulation of inflammation and protection from tissue damage. *Nature* 2001. 414: 916-920.
3 Thompson, L. F., Eltzschig, H. K., Ibla, J. C., Van De Wiele, C. J., Resta, R., Morote-Garcia, J. C. and Colgan, S. P., Crucial role for ecto-5'-nucleotidase (CD73) in vascular leakage during hypoxia. *J. Exp. Med.* 2004. 200: 1395-1405.
4 Lennon, P. F., Taylor, C. T., Stahl, G. L. and Colgan, S. P., Neutrophil-derived 5'-adenosine monophosphate promotes endothelial barrier function via CD73-mediated conversion to adenosine and endothelial A2B receptor activation. *J. Exp. Med.* 1998. 188: 1433-1443.
5 Synnestvedt, K., Furuta, G. T., Comerford, K. M., Louis, N., Karhausen, J., Eltzschig, H. K., Hansen, K. R., Thompson, L. F. and Colgan, S. P., Ecto-5'-nucleotidase (CD73) regulation by hypoxia-inducible factor-1 mediates permeability changes in intestinal epithelia. *J. Clin. Invest.* 2002. 110: 993-1002.
6 Henttinen, T., Jalkanen, S. and Yegutkin, G. G., Adherent leukocytes prevent adenosine formation and impair endothelial barrier function by Ecto-5'-nucleotidase/CD73-dependent mechanism. *J. Biol. Chem.* 2003. 278: 24888-24895.
7 Eckle, T., Fullbier, L., Wehrmann, M., Khoury, J., Mittelbronn, M., Ibla, J., Rosenberger, P. and Eltzschig, H. K., Identification of Ectonucleotidases CD39 and CD73 in Innate Protection during Acute Lung Injury. *J. Immunol.* 2007. 178: 8127-8137.
8 Niemela, J., Henttinen, T., Yegutkin, G. G., Airas, L., Kujari, A. M., Rajala, P. and Jalkanen, S., IFN-alpha induced adenosine production on the endothelium: a mechanism mediated by CD73 (ecto-5'-nucleotidase) up-regulation. *J. Immunol.* 2004. 172: 1646-1653.
9 Ohara, M., Unno, N., Mitsuoka, H., Kaneko, H. and Nakamura, S., Peritoneal lavage with oxygenated perfluorochemical preserves intestinal mucosal barrier function after ischemia-reperfusion and ameliorates lung injury. *Crit. Care Med.* 2001. 29: 782-788.
10 Yegutkin, G. G., Henttinen, T. and Jalkanen, S., Extracellular ATP formation on vascular endothelial cells is mediated by ecto-nucleotide kinase activities via phosphotransfer reactions. *Faseb J.* 2001. 15: 251-260.
11 Airas, L., Niemelä, J., Yegutkin, G. and Jalkanen, S., Mechanism of Action of IFN-β in the Treatment of Multiple Sclerosis. Ann N.Y. Acad. Sci. 1110:641-648 (2007).

The invention claimed is:
1. A method of determining a course of treatment of an inflammatory disease in a patient undergoing treatment of the inflammatory disease with an active agent that influences CD73 protein level or activity in the patient, the method comprising:
(a) identifying a patient undergoing treatment of an inflammatory disease with an agent that influences the CD73 protein level or activity in the patient, wherein the inflammatory disease is selected from the group consisting of acute lung injury, acute respiratory distress syn- drome, acute pancreatitis, multi-organ failure and systemic inflammatory response syndrome;
(b) obtaining a sample of tissue fluid from the patient at a first or earlier point in time;
(c) determining the amount of CD73 protein or the activity of the CD73 protein in the sample at the first or earlier point in time;
(d) obtaining a sample of tissue fluid from the patient at a second or subsequent point in time;
(e) determining the amount of CD73 protein or the activity of the CD73 protein in the sample at the second or subsequent point in time;
(f) comparing the amount of the CD73 protein or the activity of the CD73 protein in the sample at the second or subsequent point in time with that of the first or earlier point in time;
(g) determining the course of treatment of the patient with an agent that influences the CD73 protein level or activity in the patient from the comparison of the amount of the CD73 protein or the activity of the CD73 protein in the sample by
  (g1) continuing the treatment of the patient with an agent that influences the CD73 protein level or activity in the patient if the amount of the CD73 protein or the activity of the CD73 protein is increased at the second or subsequent point of time or
  (g2) replacing or supplementing the treatment of the patient with an agent that influences the CD73 protein level or activity in the patient by another therapy if the amount of the CD73 protein or the activity of the CD73 protein is not increased at the second or subsequent point in time;
(h) repeating steps (d)-(f); and
(i) determining the course of treatment of the patient with an agent that influences the CD73 protein level or activity in the patient from the comparison of the amount of the CD73 protein or the activity of the CD73 protein in the sample by
  (i1) continuing the treatment of the patient with an agent that influences the CD73 protein level or activity in the patient if the amount of the CD73 protein or the activity of the CD73 protein is increased at the subsequent point of time or
  (i2) stopping the treatment of the patient with an agent that influences the CD73 protein level or activity in the patient if the amount of the CD73 protein or the activity of the CD73 protein is not increased at the subsequent point in time.

2. The method according to claim 1, wherein the active agent is a cytokine or a statin.

3. The method according to claim 2, wherein the cytokine is an interferon or an interleukin.

4. The method according to claim 3, wherein the interferon is interferon-beta.

* * * * *